United States Patent [19]

Baldwin et al.

[11] Patent Number: 4,562,184

[45] Date of Patent: Dec. 31, 1985

[54] SUBSTITUTED-AMINOHYDROXY-PROPOXY-THIADIAZOLES, β-BLOCKING COMPOSITIONS AND USE

[75] Inventors: John J. Baldwin, Gwynedd Valley; Gerald S. Ponticello, Lansdale, both of Pa.

[73] Assignee: Merck & Co., Inc., Rahway, N.J.

[21] Appl. No.: 596,185

[22] Filed: Apr. 2, 1984

[51] Int. Cl.[4] ............ A61K 31/425; A61K 31/535; C07D 285/10; C07D 413/04

[52] U.S. Cl. .................... 514/222; 514/229; 514/252; 514/269; 514/316; 514/326; 514/342; 514/362; 544/58.6; 544/58.7; 544/60; 544/82; 544/114; 544/122; 544/131; 544/134; 544/238; 544/295; 544/333; 544/357; 544/360; 544/367; 544/405; 546/187; 546/193; 546/209; 546/277; 548/135

[58] Field of Search ............ 544/58.6, 58.7, 60, 544/82, 114, 122, 131, 134, 238, 295, 333, 357, 360, 367, 405; 546/187, 193, 209, 277; 548/135; 424/248.51, 250, 251, 263, 267, 270; 514/222, 229, 252, 269, 316, 326, 342, 362

[56] References Cited

U.S. PATENT DOCUMENTS

| 4,034,106 | 7/1977 | Smith | 424/304 |
| 4,134,983 | 1/1979 | Baldwin | 424/267 |
| 4,440,774 | 4/1984 | Baldwin | 424/267 |

*Primary Examiner*—Robert W. Ramsuer
*Attorney, Agent, or Firm*—Alice C. Robertson; Salvatore C. Mitri

[57] ABSTRACT

Novel substituted-aminohydroxypropoxy-thiadiazoles and pharmaceutically acceptable salts thereof exhibit β-adrenergic blocking activity.

9 Claims, No Drawings

SUBSTITUTED-AMINOHYDROXYPROPOXY-THIADIAZOLES, β-BLOCKING COMPOSITIONS AND USE

SUMMARY OF THE INVENTION

This invention is concerned with compounds having a general structural formula:

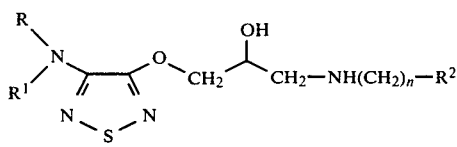

and pharmaceutically acceptable salts thereof which have β-adrenergic receptor blocking properties and are thereby valuable antihypertensive, antiarrhythmic, antiangina, and cardioprotective agents, and useful in the treatment of elevated intraocular pressure.

The invention is also concerned with novel processes for the preparation of the novel compounds; pharmaceutical formulations comprising one of the novel compounds as active ingredient; and the use of the novel compounds in the treatment of hypertension, arrhythmia, angina, post-myocardial infarction and elevated intraocular pressure.

BACKGROUND OF THE INVENTION

A class of agents known as β-adrenergic blocking agents are available which effect cardiac, vascular and pulmonary functions and can be mild antihypertensives. Specifically, these agents have the capability of reducing heart rate, counteracting vasodepression and suppressing bronchodilation. β-adrenergic blocking agents, their chemical structure and activity, are disclosed in "Clinical Pharmacology and Therapeutics" 10, 292–306 (1969) and in M. S. Large, et al., *J. Med. Chem.*, 25, 1417–1422 (1982). One β-blocker known as timolol is structurally related to the compounds of this invention and is disclosed in U.S. Pat. No. 3,655,663.

DETAILED DESCRIPTION OF THE INVENTION

The compound of this invention has structural formula:

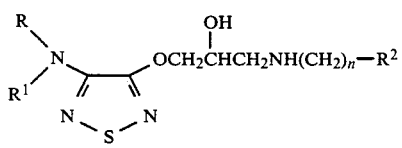

or a pharmaceutically acceptable salt thereof wherein:
n is 1, 2 or 3;
R and $R^1$ are independently
(1) $C_{1-8}$ alkyl, either straight or branched chain and either unsubstituted or substituted with:
(a) hydroxy or
(b) $C_{1-4}$ alkoxy; or
(2) R and $R^1$ are joined together directly to form, with the nitrogen to which they are attached, pyrrolidino or piperidino, or through a heteroatom selected from O, N-($C_{1-3}$ alkyl) and S to form a six-membered heterocycle such as N-($C_{1-3}$ alkyl)piperazino, or morpholino;

$R^2$ is
(1) 6-membered heterocyclic aryl, with one or two nitrogen atoms,

(2)

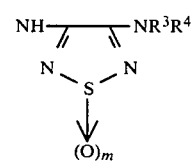

(3)

wherein m is 1 or 2, and

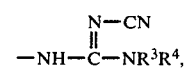

(4)

wherein
$R^3$ and $R^4$ are independently,
(a) hydrogen,
(b) $C_{1-4}$ alkyl,
(c) carbocyclic aryl such as phenyl or naphthyl, or
(d) joined together form a 5-membered ring with the nitrogen to which they are attached such as pyrrolidino,
(e) joined together either directly or through a second heteroatom selected from O, S, or N ($C_{1-4}$ alkyl) to form a 6-membered heterocycle such as piperidino, N-methylpiperazino, morpholino or the like.

In a preferred embodiment of the novel compounds n is 1 or 2; R and $R^1$ are $C_{1-8}$ alkyl, or taken together form a 6-membered heterocycle comprising 2 heteroatoms: and $R_2$ is —NHCONR$^3$R$^4$,

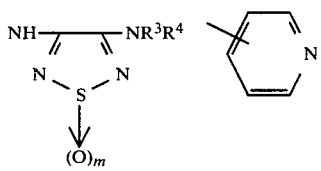

wherein $R^3$ and $R^4$ are independently hydrogen, $C_{1-4}$ alkyl, phenyl, or a 6-membered heterocycle with 1 or 2 heteroatoms.

In an even more preferred embodiment, R and $R^1$ taken together represent morpholino, n is 2 and $R^2$ is

wherein $R^3$ and $R^4$ are independently hydrogen, $C_{1-4}$ alkyl, phenyl or a 6-membered heterocycle with 2 heteroatoms.

The compounds of the present invention have as asymmetric center in the propoxy side chain and therefore are resolvable into (R)- and (S)-enantiomers. This invention includes these optical isomers and mixtures thereof, including racemic mixtures.

The compounds of the present invention also include the non-toxic pharmaceutically acceptable acid addition salts of the present compounds. The acid addition salts are prepared by treating the compounds of the invention with an appropriate amount of a suitable organic or inorganic acid. Examples of useful organic acids are carboxylic acids such as maleic, tartaric, acetic, pamoic, oxalic, propionic, salicylic, succinic, citric, malic, isethionic, or the like acids; useful inorganic acids are hydrohalo acids such as hydrochloric, hydrobromic, sulfuric, phosphoric or the like acids.

The novel compounds of this invention are generally prepared by the process disclosed in Reaction Scheme I:

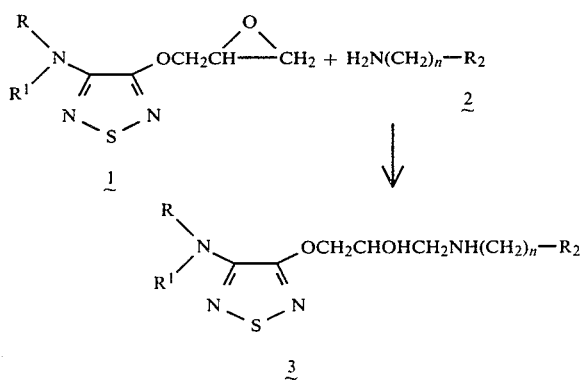

Scheme I

Reaction of epoxide 1 with an amine of type 2 at about 50°–150° C. in a suitable solvent such as methanol, ethanol, isopropanol, THF, methylenechloride, or toluene for about 1–48 hours preferably in isopropanol at about 70° C. for about 15 hours yields 3.

The majority of the amines of type 2 are prepared by known literature methods or are commercially available. However, N-(2-aminoethyl)-N'-cyano-N''-dimethylguanidine was prepared by the general method described in Scheme II.

Scheme II

[H₃CS–C(=N–CN)–SCH₃  +  HN(R₃)(R₄)] → 4  5

[H₃CS–C(=N–CN)–N(R₃)(R₄)] + H₂N(CH₂)ₙNH₂ → 6  7

-continued
Scheme II

[H₂N(CH₂)ₙNH–C(=N–CN)–N(R₃)(R₄)]
8

As shown in Scheme II, the dithiomethyl derivative 4 is reacted with an amine of type 5 in a suitable solvent such as methanol, ethanol, isopropanol, methylene chloride, ether, THF, toluene, or the like, at 0° C. to the reflux temperature of the solvent for 5 minutes to 24 hours, preferably in isopropanol at ambient temperature for 15 minutes to yield 6. After the reaction is essentially complete, the reaction mixture is added to a solution of diamine 7 in a suitable solvent such as isopropanol (or others as described above), at 0° C. to the reflux temperature of the solvent for 1–48 hours preferably in isopropanol at ambient temperature for 4 hours to yield 8.

The ureas, on the other hand are prepared in accordance with reaction III:

Scheme III

H₂N–CH₂CH₂–NH₂ + OCNR³ → H₂N–CH₂CH₂–N(H)–C(=O)–NR³H

The isocyanate is added slowly to ethylenediamine in a suitable solvent such as those itemized in the description of Reaction Scheme I, at about 0° C. to the reflux temperature of the solvent, preferably about room temperature. Times of about 1 to 24 hours are adequate to complete the reaction, and usually about 2–4 hours.

To prepare those novel compounds wherein $R^2$ is

[thiadiazole with NH and NR³R⁴ substituents, (O)ₘ]

the reactions of Scheme IV may be employed.:

Scheme IV

[thiadiazole-OCH₂CH(OH)CH₂N(R)–(CH₂)ₙNH +  diethoxy-thiadiazole (O)ₘ]

-continued
Scheme IV

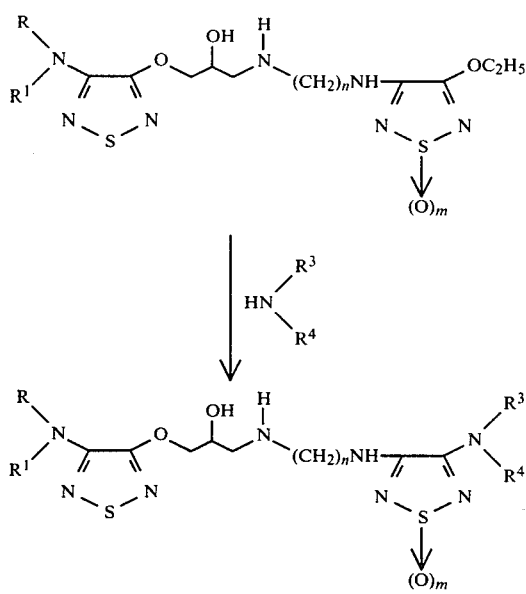

The first step is conducted in an appropriate solvent such as a $C_{1-3}$ alkanol, especially isopropanol, or methylene chloride, THF or toluene for about 1 to 48 hours at about 0° C. to the reflux temperature of the solvent, preferably for about one hour at about room temperature.

The second step of Scheme IV is conveniently conducted by adding the amine, $HNR^3R^4$ directly to the reaction mixture of the first step. Stirring is continued for another 1 to 24 hours at 0° C. to reflux, preferably at about room temperature for about one hour.

The β-adrenergic blocking activity of the compounds of the present invention indicates that they are useful in the treatment of warm blooded animals, including humans suffering from conditions such as hypertension, angina pectoris, elevated intraocular pressure or certain arrhythmias which are known to be amenable to treatment with β-adrenergic blocking agents. They are also cardioprotective agents useful in the chronic treatment of post-myocardial infarction.

The compounds of this invention can be administered orally or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for parenteral administration; e.g., dissolved or dispersed in a suitable liquid carrier as a solution, suspension or emulsion; or (c) for topical administration in a patch or as an aerosol. The ratio of active compound to compounding ingredients; i.e., carrier, diluent, etc., will vary as the dosage form requires. Generally, doses of the present compounds of from about 0.01 to about 50 mg/kg and preferably from about 0.1 to about 20 mg/kg of body weight per day may be used. Dosage may be single or multiple depending on the daily total required and the unit dosage.

Following are examples illustrating representative pharmaceutical formulations containing compounds of the present invention. Conventional techniques are used to prepare these formulations.

| TABLET FORMULATION 1 | |
|---|---|
| INGREDIENT | AMOUNT (Mg.) |
| 3-[3-[[2-[(Dimethylaminocyanoiminomethyl)amino]ethyl]amino]-2-hydroxypropoxy]-4-morpholino-1,2,5-thiadiazole | 40.0 |
| calcium phosphate | 120.0 |

| CAPSULE FORMULATION | |
|---|---|
| INGREDIENT | AMOUNT (Mg.) |
| 1-(n-Butyl)-3-[2-[[2-hydroxy-3-[[[4-(N—morpholino)-3-(1,2,5-thiadiazolyloxy]]]propylamino]]ethyl]urea | 250 |
| lactose, U.S.P. | 93 |
| talc | 7 |

| INJECTABLE SOLUTION | |
|---|---|
| INGREDIENT | AMOUNT (Mg.) |
| 1-Phenyl-3-[2-[[2-hydroxy-3-[[[4-(N—morpholino)-3-(1,2,5-thiadiazolyloxy]]] propylamino]]ethyl]urea | 5 |
| sodium chloride | 9 |
| distilled water, q.s. 1.0 ml. | |

| LIQUID SUSPENSION | |
|---|---|
| INGREDIENT | AMOUNT (Mg.) |
| 3-[2-Hydroxy-3-[2-(2-pyridyl) ethylamino]propoxy]-4-[N—morpholino]-1,2,5-thiadiazole | 5.0 |
| Veegum H.V. | 3.0 |
| methyl parable | 1.0 |
| kaolin | 10.0 |
| glycerin | 250.0 |
| water, q.s. 1 liter | |

The following examples illustrate preparation of representative compounds of the present invention.

EXAMPLE 1

3-[3-[[2-[(Dimethylaminocyanoiminomethyl)amino]ethyl]amino]-2-hydroxypropoxy]-4-morpholino-1,2,5-thiadiazole

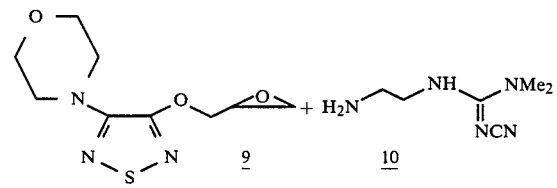

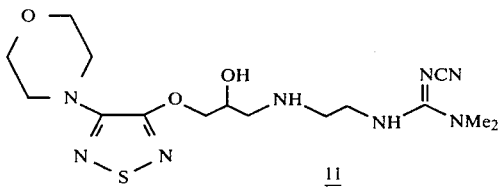

The epoxide 9 (1.70 g, 7 mmole) and the amino derivative 10 in isopropanol (20 ml) were heated at 50° C. with stirring. After 5 hours the solvent was removed in vacuo and the crude product purified by chromatography on silica gel 60 using CH$_2$Cl$_2$—CH$_3$OH—H$_2$O (80-20-2 v/v/v) as the eluant. Product (1.07 g) was rechromatographed on silica gel 60 using CHCl$_3$—CH$_3$OH—H$_2$O (90-10-1 v/v/v) as the eluant. Crystallization from 20 ml CH$_3$CN at −15° C. yielded 600 mg (22%) of 11, m.p. 141°–143° C.

EXAMPLE 2

1-(n-Butyl)-3-[2-[[2-hydroxy-3-[[[4-(N-morpholino)-3-(1,2,5-thiadiazolyloxy]]]propylamino]]ethyl]urea

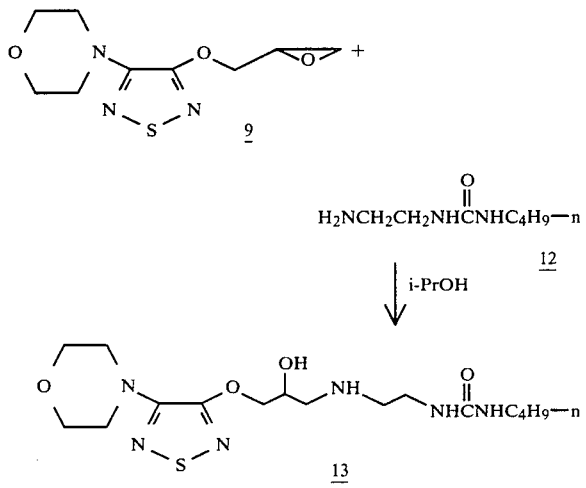

Step A: Preparation of 1-(n-Butyl)-3-(2-aminoethyl)urea

A solution of n-butylisocyanate (19.83 g, 0.2 m) in ether (50 ml) was added over 40 minutes to a vigorously stirred solution of ethylenediamine (48.08 g, 0.8 m) in isopropanol (1000 ml). After stirring at 25° C. for 3 hours and standing for 16 hours, the mixture was filtered and the filtrate evaporated to dryness under reduced pressure initially using water aspiration and finally high vacuum at 70° C. The residue was stirred for 1 hour in 12N HCl (20 ml) and H$_2$O (200 ml), filtered and the filtrate was rendered alkaline with 40% NaOH and evaporated to dryness under reduced pressure. The residue was chromatographed on silica gel and eluted with 20% CH$_3$OH—CHCl$_3$ saturated with NH$_3$ to give 12 (18.7 g, 59%).

Step B: Preparation of 1-(n-Butyl)-3-[2-[[2-hydroxy-3-[[[4-(N-morpholino)-3-(1,2,5-thiadiazolyloxy]]]propylamino]]ethyl]urea A mixture of 3-(2,3-epoxy-1-propoxy)-4-morpholino-1,2,5-thiadiazole (2.03 g, 0.0083 m) and 1-(n-butyl)-3-(2-aminoethyl)urea (1.91 g, 0.012 m) in isopropanol (45 ml) was stirred at 70° C. for 70 hours. The solvent was evaporated under reduced pressure and the residue was chromatographed on silica gel and eluted with 10% CH$_3$OH—CHCl$_3$ saturated with NH$_3$ to give 13 (2.02 g, 60%). An analytical sample had m.p. 152°–153.5° C. after recrystallization from acetonitrile.

EXAMPLE 3

1-Phenyl-3-[2-[[2-hydroxy-3-[[[4-(N-morpholino)-3-(1,2,5-thiadiazolyloxy]]]propylamino]]ethyl]urea

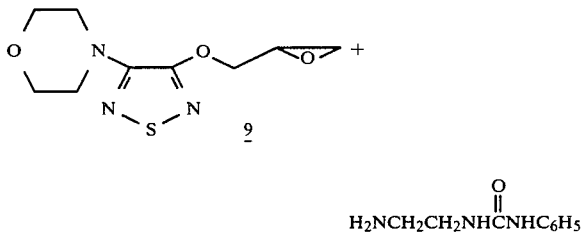

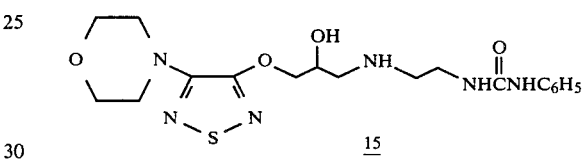

Step A: Preparation of 1-Phenyl-3-(2-aminoethyl)urea, 14

Compound 14 was prepared as described for 1-(n-butyl)-3-(2-aminoethyl)urea (Example 2, Step A) starting with phenylisocyanate (23.82 g, 0.2 m), ether (50 ml), ethylenediamine (48.08 g, 0.8 m) and isopropanol (1000 ml). The product was obtained in 9.5% yield (3.40 g, m.p. 104°–107° C.). An analytical sample melted at 105°–108° C. after recrystallization from CHCl$_3$.

Step B: Preparation of 1-Phenyl-3-[2-[[2-hydroxy-3-[[[4-(N-morpholino)-3-(1,2,5-thiadiazolyl-oxy]]]-propylamino]]ethyl]urea, 15

A mixture of 3-(2,3-epoxy-1-propoxy)-4-morpholino-1,2,5-thiadiazole (1.61 g, 0.0066 m) and 14 (1.70 g, 0.0095 m) in isopropanol (35 ml) was stirred at 70° C. for 22.5 hours. The solvent was evaporated under reduced pressure and the residue was chromatographed on silica gel and eluted with 10% CH$_3$OH—CHCl$_3$ saturated with NH$_3$ to yield 15 (1.55 g, 56%). An analytical sample melted at 131°–132° C. after recrystallization from acetonitrile.

EXAMPLE 4

3-[2-Hydroxy-3-[2-(2-pyridyl)ethylamino]propoxy]-4-[N-morpholino]-1,2,5-thiadiazole, 17

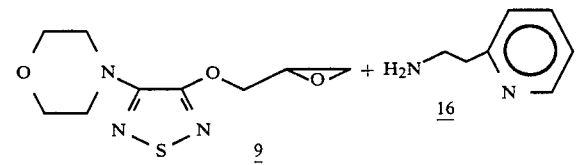

-continued

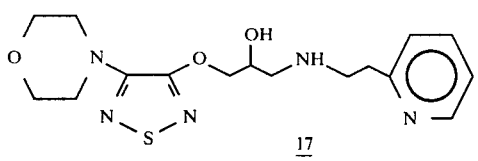

17

The epoxide 9 (3.65 g, 15 mmole) was dissolved in a mixture of 2-propanol (20 ml) and $CH_2Cl_2$ (20 ml) and added dropwise to a stirred solution of 16 (2.01 g, 16.5 mmole) in 2-propanol (10 ml) at 60° C. The reaction mixture was stirred at 60° C. for 19 hours, the solvent removed in vacuo and the residue chromatographed on silica gel 60 (230-400 mesh) using $CHCl_3$—$CH_3OH$—$NH_4OH$ (90:10:1) as the eluant. The effluant containing the product was evaported to dryness in vacuo and the residue crystallized on standing. The crystals were washed with hexanes and dried in vacuo to yield 3.1 g (57%) of 17, m.p. 109°-110°. Analysis satisfactory for $C_{16}H_{23}N_5O_3S$.

EXAMPLE 5

3-[2-Hydroxy-3-[2-(4-pyridyl)ethylamino]propoxy]-4-[N-morpholino]-1,2,5-thiadiazole This compound was prepared as described in Example 4 except that (4-pyridyl)ethylamine was used as starting material, and the product had m.p. 79°-80° C.; (20% yield); Analysis satisfactory for $C_{16}H_{23}N_5O_3S$.

EXAMPLE 6

3-[2-Hydroxy-3-[2-(3-pyridyl)ethylamino]propoxy]-4-[N-morpholino]-1,2,5-thiadiazole This compound was prepared as described in Example 4 except that (3-pyridyl)ethylamine was used as starting material. It had mp 114°-115° C. (35% yield); Analysis satisfactory for $C_{16}H_{23}H_5O_3S$.

Employing the procedures substantially as described in Examples 1 through 6 the following compounds are prepared in accordance with Reaction Scheme I, or Schemes I and IV in the cases of (f) and (g) of the following Table:

General structure:
$R, R^1$-N-[thiadiazole]-$OCH_2CHOHCH_2NH(CH_2)_n$-$R^2$

| | R | $R^1$ | n | $R^2$ |
|---|---|---|---|---|
| (a) | —$CH_3$ | —$CH_3$ | 2 | pyridazinyl (N=N) |
| (b) | —$CH_2CH_3$ | —$CH_2CH_3$ | 2 | pyridyl |
| (c) | —$CH(CH_3)_2$ | —$CH(CH_3)_2$ | 1 | NHCON-morpholino |
| (d) | —$CH_2CH_2OH$ | —$CH_2CH_2OH$ | 3 | pyrazinyl |
| (e) | —$CH_2CH_2OCH_3$ | —$CH_2CH_2OCH_3$ | 3 | NHCON-morpholino |
| (f) | —$CH_2CH_2$—$CH_2CH_2$— | | 1 | —HN-[thiadiazole S-oxide]-$N(CH_3)_2$ |
| (g) | —$CH_2CH_2$—O—$CH_2CH_2$— | | 2 | —HN-[thiadiazole S,S-dioxide]-$NHCH_3$ |

-continued

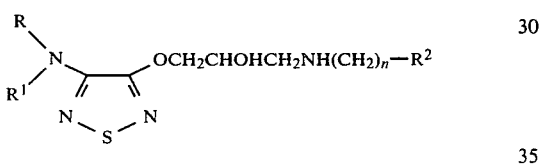

| | R | R¹ | n | R² |
|---|---|---|---|---|
| (h) | —CH₂—CH₂—N(CH₂CH₃)—CH₂CH₂— | | 3 | pyridazinyl |
| (i) | —CH₂CH₂—S—CH₂CH₂— | | 2 | pyrimidinyl |
| (j) | —CH₃ | —CH₃ | 1 | pyrazinyl |

What is claimed is:

1. A compound of structural formula:

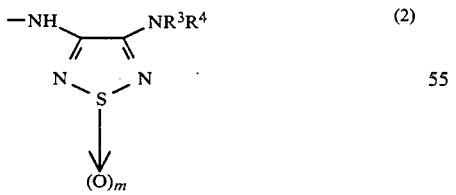

or a pharmaceutically acceptable salt thereof wherein:
n is 1, 2 or 3;
R and R¹ are independently
(1) $C_{1-8}$ alkyl, either straight or branched chain and either unsubstituted or substituted with:
  (a) hydroxy or
  (b) $C_{1-4}$ alkoxy; or
(2) R and R¹ are joined together directly to form, with the nitrogen to which they are attached, pyrrolidino or piperidino, or through a heteroatom selected from O, N ($C_{1-3}$ alkyl) and S to form a six-membered heterocyle;
R² is
(1) 6-membered heterocyclic aryl, with one or two nitrogen atoms,

wherein m is 1 or 2, or $$-NH-\overset{N-CN}{\underset{\|}{C}}-NR^3R^4, \quad (3)$$

wherein $R^3$ and $R^4$ are independently,
(a) hydrogen,
(b) $C_{1-14}$ alkyl,
(c) carbocyclic aryl, or
(d) joined together, $R^3$ and $R^4$ form a 5-membered ring with the nitrogen to which they are attached, or
(e) joined together $R^3$ and $R^4$, either directly or through a second heteroatom selected from O, S, and N-($C_{1-4}$ alkyl), form a 6-membered heterocycle.

2. The compound of claim 1 or a pharmaceutically acceptable salt thereof wherein:
n is 1 or 2;
R and R¹ are independently:
(1) $C_{1-8}$ alkyl, or
(2) taken together a 6-membered heterocycle comprising 2 heteroatoms; and
R² is

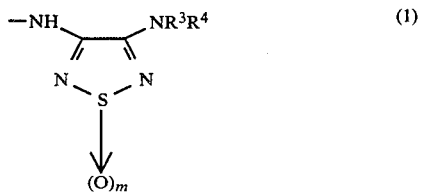

wherein m is 1 or 2, $$-NH-\overset{N-CN}{\underset{\|}{C}}-NR^3R^4; \quad (2)$$

wherein $R^3$ and $R^4$ are independently,
(a) hydrogen,
(b) $C_{1-4}$ alkyl,
(c) phenyl, or
(d) 6-membered heterocycle with 2 heteroatoms,
(3) pyridyl, or
(4) pyrazinyl.

3. The compound of claim 2 or a pharmaceutically acceptable salt thereof, wherein: R and $R^1$ taken together represent morpholino; n is 2; and $R^2$ is

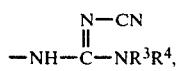

or pyridinyl, wherein $R^3$ and $R^4$ are independently hydrogen, $C_{1-4}$ alkyl, phenyl, or 6-membered heterocycle with 2 heteroatoms.

4. A pharmaceutical β-blocking formulation comprising a pharmaceutically acceptable carrier and an effective β-blocking amount of a compound of structural formula;

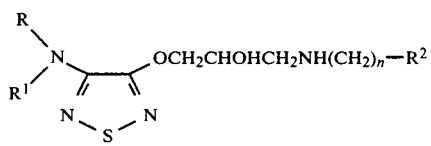

or a pharmaceutically acceptable salt thereof wherein:
n is 1, 2 or 3;
R and $R^1$ are independently
 (1) $C_{1-8}$ alkyl, either straight or branched chain and either unsubstituted or substituted with:
  (a) hydroxy or
  (b) $C_{1-4}$ alkoxy; or
 (2) R and $R^1$ are joined together directly to form, with the nitrogen to which they are attached, pyrrolidino or piperidino, or through a heteroatom selected from O, N ($C_{1-3}$ alkyl) and S to form a six-membered heterocyle;
$R^2$ is
 (1) 6-membered heterocyclic aryl, with one or two nitrogen atoms,

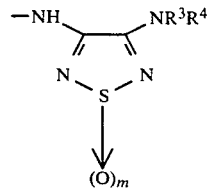

wherein m is 1 or 2, or

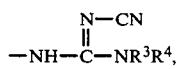

wherein $R^3$ and $R^4$ are independently,
 (a) hydrogen,
 (b) $C_{1-4}$ alkyl,
 (c) carbocyclic aryl, or
 (d) joined together $R^3$ and $R^4$ form a 5-membered ring with the nitrogen to which they are attached, or
 (e) joined together $R^3$ and $R^4$, either directly or through a second heteroatom selected from O, S, and N ($C_{1-4}$ alkyl), form a 6-membered heterocycle.

5. The formulation of claim 4 wherein;
n is 1 or 2;
R and $R^1$ are independently:
 (1) $C_{1-8}$ alkyl, or
 (2) taken together a 6-membered heterocycle comprising 2 heteroatoms; and
$R^2$ is

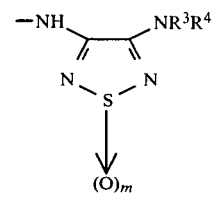

wherein m is 1 or 2,

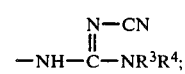

wherein
$R^3$ and $R^4$ are independently,
 (a) hydrogen,
 (b) $C_{1-4}$ alkyl,
 (c) phenyl, or
 (d) 6-membered heterocycle with 2 heteroatoms,
 (3) pyridyl, or
 (4) pyrazinyl.

6. The formulation of claim 5, wherein; R and $R^1$ taken together represents morpholino; n is 2; and $R^2$ is

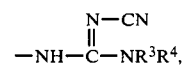

or pyridinyl wherein $R^3$ and $R^4$ are independently hydrogen, $C_{1-14}$ alkyl, phenyl, or 6-membered heterocycle with 2 heteroatoms.

7. A method of treatment wherein β-blockade is indicated which comprises the administration to a patient in need of such treatment of an effective β-blocking amount of a compound of structural formula:

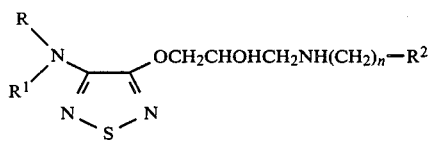

or a pharmaceutically acceptable salt thereof wherein:
n is 1, 2 or 3;
R and $R^1$ are independently
 (1) $C_{1-8}$ alkyl, either straight or branched chain and either unsubstituted or substituted with:
  (a) hydroxy or
  (b) $C_{1-4}$ alkoxy; or
 (2) R and $R^1$ are joined together directly to form, with the nitrogen to which they are attached, pyrrolidino or piperidino, or through a heteroatom selected from O, N ($C_{1-3}$ alkyl) and S to for a six-membered heterocycle;
$R^2$ is
 (1) 6-membered heterocyclic aryl, with one or two nitrogen atoms,

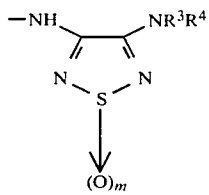

wherein m is 1 or 2, or

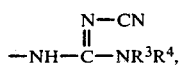 (3)

wherein $R^3$ and $R^4$ are independently,
 (a) hydrogen,
 (b) $C_{1-4}$ alkyl,
 (c) carbocyclic aryl, or
 (d) joined together $R^3$ and $R^4$ form a 5-membered ring with the nitrogen to which they are attached, or
 (e) joined together $R^3$ and $R^4$, either directly or through a second heteroatom selected from O, S, and N-($C_{1-4}$ alkyl) form a 6-membered heterocycle.

8. The method of claim 7 wherein:
n is 1 or 2;
R and $R^1$ are independently:
 (1) $C_{1-8}$ alkyl, or
 (2) taken together a 6-membered heterocycle comprising 2 heteroatoms; and $R^2$ is

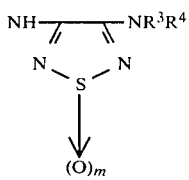 (1)

wherein m is 1 or 2,

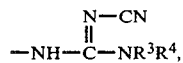 (2)

wherein $R^3$ and $R^4$ are independently,
 (a) hydrogen,
 (b) $C_{1-4}$ alkyl,
 (c) phenyl, or
 (d) 6-membered heterocycle with 2 heteroatoms,
 (3) pyridyl, or
 (4) pyrazinyl.

9. The method of claim 8 wherein; R and $R^1$ taken together represent morpholino; n is 2; and $R^2$ is $$-NH-\overset{N-CN}{\underset{\parallel}{C}}-NR^3R^4,$$

or pyridinyl wherein $R^3$ and $R^4$ are independently hydrogen, $C_{1-4}$ alkyl, phenyl, or 6-membered heterocycle with 2 heteroatoms.

* * * * *